(12) United States Patent
Clancy et al.

(10) Patent No.: US 11,866,679 B2
(45) Date of Patent: Jan. 9, 2024

(54) SYSTEM, METHOD, PROCESS AND NUTRIENT-RICH PRODUCT DERIVED FROM WINE DERIVATIVES

(71) Applicant: CRUSH DYNAMICS INC., Vancouver (CA)

(72) Inventors: Sean Clancy, Summerland (CA); Gary Strachan, Summerland (CA); William Leslie Broddy, Summerland (CA)

(73) Assignee: Crush Dynamics Inc., Summerland (CA)

( * ) Notice: Subject to any disclaimer, the term of this patent is extended or adjusted under 35 U.S.C. 154(b) by 0 days.

(21) Appl. No.: 18/056,716

(22) Filed: Nov. 17, 2022

(65) Prior Publication Data

US 2023/0183622 A1 Jun. 15, 2023

Related U.S. Application Data

(63) Continuation of application No. 16/882,317, filed on May 22, 2020, now Pat. No. 11,584,904.

(60) Provisional application No. 62/852,295, filed on May 23, 2019.

(51) Int. Cl.
| | | |
|---|---|---|
| A61K 36/00 | (2006.01) |
| C12F 3/06 | (2006.01) |
| C12G 1/00 | (2019.01) |
| A23L 33/105 | (2016.01) |
| A23L 33/145 | (2016.01) |
| A23L 5/43 | (2016.01) |
| A61K 8/9789 | (2017.01) |
| A61Q 19/00 | (2006.01) |
| A23L 27/12 | (2016.01) |

(52) U.S. Cl.
CPC .............. *C12F 3/06* (2013.01); *A23L 5/43* (2016.08); *A23L 27/12* (2016.08); *A23L 33/105* (2016.08); *A23L 33/145* (2016.08); *A61K 8/9789* (2017.08); *A61Q 19/00* (2013.01); *C12G 1/005* (2013.01); *A23V 2002/00* (2013.01); *A61K 2800/10* (2013.01)

(58) Field of Classification Search
CPC ............... A61K 2800/85; C12F 3/06
See application file for complete search history.

(56) References Cited

PUBLICATIONS

Hong et al., Optimization of fermentation process and physicochemical properties of probiotic fermented grape pomace. Shipin Kexue / Food Science (2019), vol. 40, No. 8, pp. 63-72 (Year: 2019).*

* cited by examiner

*Primary Examiner* — Qiuwen Mi
(74) *Attorney, Agent, or Firm* — Elman IP; Gerry J. Elman

(57) ABSTRACT

Described herein is a system, methods, processes and nutrient-rich products-by-process, which are generated by the conversion of winery derivatives into nutrient-rich products in an ecological manner. Integration of this system into a winery assists the winery to manage its previously-considered waste nutrient-rich products in an ecological manner, which can also optionally provide them with a novel revenue stream. The system, methods, and processes are used to convert winemaking derivatives into bioactive nutrient-rich products comprising antioxidants and other bioactive molecules that reside within the marc and lees. These nutrient-rich products can be used as natural flavour, texture and color enhancers, in addition to nutritional ingredients to fortify processed foods and consumer recipes. They can also be used as health supplements and in the cosmetic industry.

20 Claims, 12 Drawing Sheets

Table I

| Stage. | Business Activities | Winery Activities | Cellar Hand Time/Container |
|---|---|---|---|
| I | The business drops processing containers at the winery prior to crush. | Unload and stack empty processing containers | Approximately 5 minutes x the number of containers |
| II | | Dump marc into processing container | Approximately 2 minutes longer than dumping in steel waste bin x the number of containers |
| III | Add lees and proprietary starter mix. | Reserve lees from first rack | Generally, less than normal time for disposal |
| IV | | Place processing containers in processing location | Approximately 5 minutes x the number of containers |
| V | | Have cellar-hand periodically check PH / Brix. Advise Company if 'stuck'. | Approximately 3 minutes x the number of containers x 5 tests |
| VI | Pick up containers when ready for finishing. | Assist with removal of containers from winery (forklift onto Company vehicle). | Approximately 5 minutes X the number of containers |
| | Total cellar hand time per container | | Approximately 45 minutes in total (±25%)/processing container: 6 minutes prior to crush 3 minutes during press 36 minutes after press |

FIG. 11

SYSTEM, METHOD, PROCESS AND NUTRIENT-RICH PRODUCT DERIVED FROM WINE DERIVATIVES

CROSS-REFERENCE TO RELATED APPLICATIONS

This is a continuing application in the nature of a divisional of U.S. patent application Ser. No. 16/882,317 filed May 22, 2020, which claims priority benefit to non-provisional U.S. patent application 62/852,295 filed May 23, 2019, each being hereby incorporated by reference.

FIELD

This disclosure pertains to the field of fermenting wine derivatives into useful nutrient-rich products.

SUMMARY

Described herein is a system, methods, processes and nutrient-rich product-by-process, which are generated by the conversion of winery derivatives into nutritionally beneficial supplements in an ecological manner. Integration of this system into a winery assists the winery to manage its previously-considered waste nutrient-rich products in an ecological manner, which can optionally bring them a novel separate novel revenue stream. The system, methods, and processes are used to convert winemaking derivatives into nutrient-rich products comprising antioxidants and other bioactive molecules, which reside within the marc and lees. These nutrient-rich products can be used as natural flavour, texture and color enhancers, in addition to nutritional ingredients to fortify processed foods and consumer recipes. They can also be used as health supplements and in the cosmetic industry,

BACKGROUND

The winemaking industry produces millions of tons of leftovers and residues, which represent an ecological and economical waste management issue for the wineries. The leftovers and residues include organic wastes, inorganic wastes, wastewater, and emission of greenhouse gases ($CO_2$, volatile organic compounds, etc.) Due to growing issues around groundwater and soil contamination, wineries send most of it to the landfill, costing the winery fees for bin drop-off, removal, haulage and tipping fees in addition to winery management costs. Addressing these issues in an appropriate manner places a financial burden on most of the wineries, especially the smaller ones.

One resource often used by winemaking industry is the intermediate bulk container (IBC), which are also known as an IBC tote, IBC tank, IBC, or pallet tank. IBCs are ideal for storing and transporting nutrient-rich products such as liquids, semi-solids, pastes, solvents, or granulate substances (food, chemicals, pharmaceuticals, etc.) in large quantities. The concept of the IBC was patented in 1993, and is described in U.S. Pat. No. 5,260,414, of which there are two main categories: flexible IBCs and rigid IBCs.

Rigid IBCs are stackable, reusable, versatile containers with an integrated pallet base mount that provides forklift and/or pallet jack maneuverability. Most IBCs are cube-shaped and this cube-shaped engineering contributes to the packaging, stacking, storing, shipping, and overall space efficiency of intermediate bulk containers. Almost all rigid IBCs are designed so they can be stacked vertically one atop the other using a forklift.

The support structure/containers can be made from metal (stainless steel), plastic (high-density polyethylene), or a composite construction (galvanized steel and plastic) of the two materials. The IBC tank can be made of plastic, stainless steel, and carbon steel tanks The IBC tank capacities generally used are often 1,040 and 1,250 litres (275 and 330 US gal).

The most widely utilized and known IBC is the limited re-use, caged IBC tote container. Caged IBC totes are composite intermediate bulk containers—a white/translucent plastic container (typically high-density polyethylene) contained and protected by a tubular galvanized steel grid, common. Most have a built-in tap (valve, spigot, or faucet) at the base of the container to which hoses can be attached, or through which the contents can be poured into smaller containers.

The winemaking process generates two major residues, which can be harvested. The major residues from the winemaking process after the de-stemming and crush steps are known as derivatives. Derivatives comprise grape marc (pomace) and lees. For every two bottles of wine made, typically the equivalent of one bottle of derivatives is produced. Winery derivatives comprise:
  a) marc (pomace) consisting of grape skin, grape pulp and grape seed derived from varietal grapes, which have been crushed and pressed as part of the winemaking process; and
  b) lees consisting of spent wine yeast, tartaric acid, grape skin pigment and grape pulp sediment, which have been extruded from the wine after fermentation and again after aging.

Grape marc provides substantial nutritional potential as supplements and to fortify food. For example, 15 grams (~1 tbsp.) of powdered derivative may contain up to 900 mg of phenols, 150 mg of tannins (catechin), 2000 mg of protein, 180 mg of potassium, 120 mg of magnesium, 4 mg of iron, 4% DV of riboflavin, 125% DV of vitamin E and 3% DV of vitamin K).

In general, wine lees is residue that forms at the bottom of wine containers consisting of: 1) first and second-fermentation lees, which are formed during the alcoholic and malolactic fermentations, respectively (herein, lees); 2) during storage or after treatments (herein, first-rack lees); and 3) aging wine lees formed during wine aging in wood barrels collected after the filtration or centrifugation of the wine (herein, second-rack lees), The main characteristics of wine lees are acidic pH (between 3 and 6), a chemical oxygen demand above 30,000 mg/L, potassium levels around 2500 mg/L, and phenolic compounds in amounts up to 1000 mg/L Approximately 30% of red wine lees are protein that is produced from yeast cell wall material, which contains 30-60% 3-b-D-glucan in dry weight.

Derivatives are used in livestock and poultry feed to extend the shelf-life of milk, dairy by-nutrient-rich products, and meat. There is extensive research on the anti-microbial benefits as a replacement for antibiotics for poultry and livestock. There is even research showing that it can cut bovine methane emissions by 30%

Although there is an identified market for these derivatives, the current processes used to transform it into shelf-stable nutrient-rich products creates a carbon footprint, is prohibitively expensive and causes significant loss in the quality in the derivatives.

The extraction of useful nutrient-rich products from wine derivatives is known in the art. However, most of these processes seek to isolate a specific compound, require multiple steps, and/or require drying the nutrient-rich product into a powder that can be easily sold in capsule, tablet, powder form, etc. Drying the nutrient-rich product and/or using chemical processes to isolate nutrient-rich products therefrom can diminish the bioavailability of the biomolecules desired in the final nutrient-rich products.

It is widely recognized that the nutrient value of foods has been diminishing since at least the 1950's, such that a need has developed for cost effective strategies to fortifying foods in the food supply, incorporating the resources of a winery to make adaptation easily accessible for the business.

There is tremendous value in monetizing these derivatives. The issue today is economics; finding a cost-effective way to process derivatives in an ecological manner, without losing flavour and nutrition.

BRIEF DESCRIPTION OF THE FIGURES

FIG. 11 provides one example of one embodiment illustrating the integration of the system with the work-flow of a winery.

DETAILED DESCRIPTION

Figure 1:
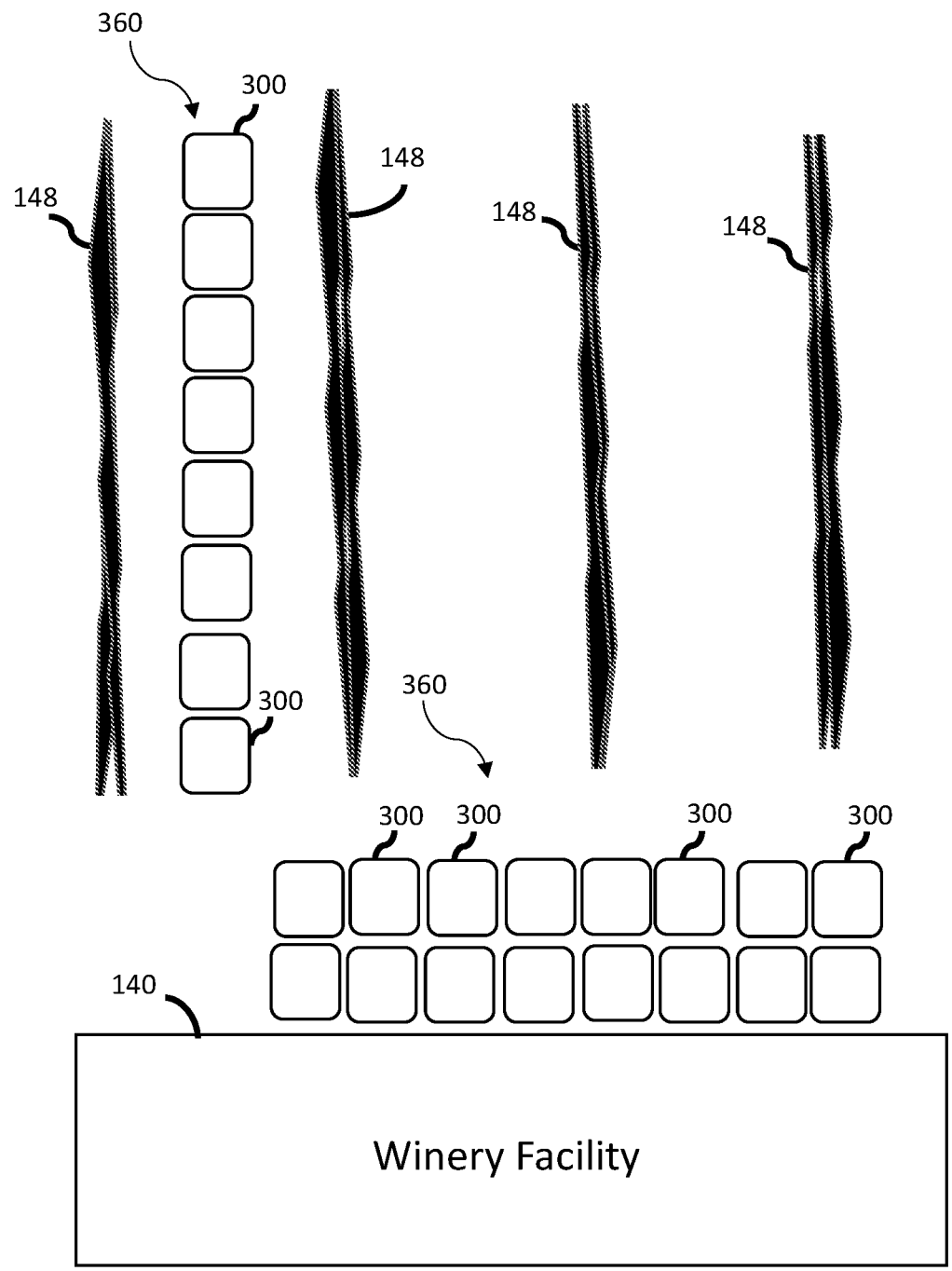
FIG. 1 provides an aerial view of one embodiment of the system, illustrating one aspect of the integration of the system into a winery.

Described herein is a system, methods, processes and nutrient-rich products-by-process, which are generated by the conversion of winery derivatives into nutritionally beneficial supplements in an ecological manner. Integration of this system into a winery assists the winery to manage its previously-considered waste nutrient-rich products in an ecological manner, which can optionally provide them a novel revenue stream. The system, methods, and processes are used to convert winemaking derivatives into bioactive nutrient-rich products comprising antioxidants and other bioactive molecules that reside within the marc and lees. These nutrient-rich products can be used as natural flavour, texture and color enhancers, in addition to nutritional ingredients to fortify processed foods and consumer recipes. They can also be used as health supplements.

One embodiment comprises a system for integration into a wine-making facility and its processes comprising: one or more processing containers, designed for ease of use by winery staff, ease of storage during processing, efficacy, monitoring and security of derivative-conversion process to at least the stage of fermented puree; instructions for the role of winery staff to participate in the process of derivative-conversion into fermented puree; and optionally, microbial formulations designed to meet the fermentation objectives of a nutrient-rich product generated by the derivative-conversion process. One embodiment of the system comprises the one or more processing containers in which a version of a food-grade intermediate bulk container has been modified by generating a retractable lid therein. One embodiment of the system comprises one or more processing containers which have been modified by incorporating aerating means attached thereto. One embodiment of the system comprises one or more processing containers which have been modified by incorporating process monitoring means attached thereto.

One embodiment of the process for converting marc, first-rack lees and optionally second-rack lees derived from the winemaking process into refined nutrient-rich products comprises the steps of: a) transferring marc to a processing container; b) hydrating marc until berries swell; c) grinding hydrated marc to generate meal; d) optionally inoculating meal with a microbial formulation; e) fermenting inoculated meal to generate fermenting meal; f) transferring first-rack lees to the processing container; g) emulsifying the first first-rack lees and fermenting meal to generate a puree; h) optionally inoculating the puree; i) fermenting said puree to generate a fermented puree; j) refining fermented puree to generate a refined nutrient-rich product; k) optionally stabilizing refined product to generate stabilized nutrient-rich product; and l) optionally packaging the stabilized nutrient-rich product. One embodiment of the process comprises inoculating with the microbial formulation selected from *Acetobacter*, and/or *Gluconobacter* and/or other known acetic acid bacteria and/or fungus inoculants. One embodiment of the process incorporates the use of enzymes, which may be added the fermenting meal. One embodiment of the process according to claim 4, wherein methane emissions that would otherwise be caused by disposal of marc and lees in buried landfills is eliminated or significantly reduced. One embodiment of the process includes a nutrient-rich product substantially produced thereby. One embodiment of the process includes the nutrient-rich product comprises varietal grape skin, varietal grape seed, and winemaking sediment.

One embodiment of the method of converting winery derivatives into bioactive products comprising the steps of: a) a business delivers one or more processing containers to a winery prior to crush; b) winery staff transfers marc to one or more processing container(s); c) winery staff rehydrates marc until berries swell, grinds the biomass into a meal, inoculates with microbials, and allows it to ferment at the winery facility; d) winery staff transfers first-rack lees to the one or more processing containers comprising fermenting meal; e) winery staff emulsifies the first-rack lees and fermenting meal to generate puree, inoculates the puree and allows it to ferment at winery facility; f) winery staff monitors the progress of fermenting puree and notifies the company when the fermentation has completed; and g) the business picks up the one or more processing containers and continues processing the fermented puree at the company facility. One embodiment of the method comprises using *Acetobacter*, and/or *Gluconobacter* and/or other known acetic acid bacteria and/or fungus inoculants in the microbial formulation. One embodiment of the method comprises the use of enzymes, which may be added the fermenting meal. One embodiment of the method comprises eliminating or significantly reducing methane emissions that would otherwise be caused by disposal of marc and lees in buried landfills. One embodiment of the method comprises a nutrient-rich product substantially produced by the method. One embodiment of the method comprises a nutrient-rich product comprising varietal grape skin, varietal grape seed, and winemaking sediment made thereby.

Figure 2:
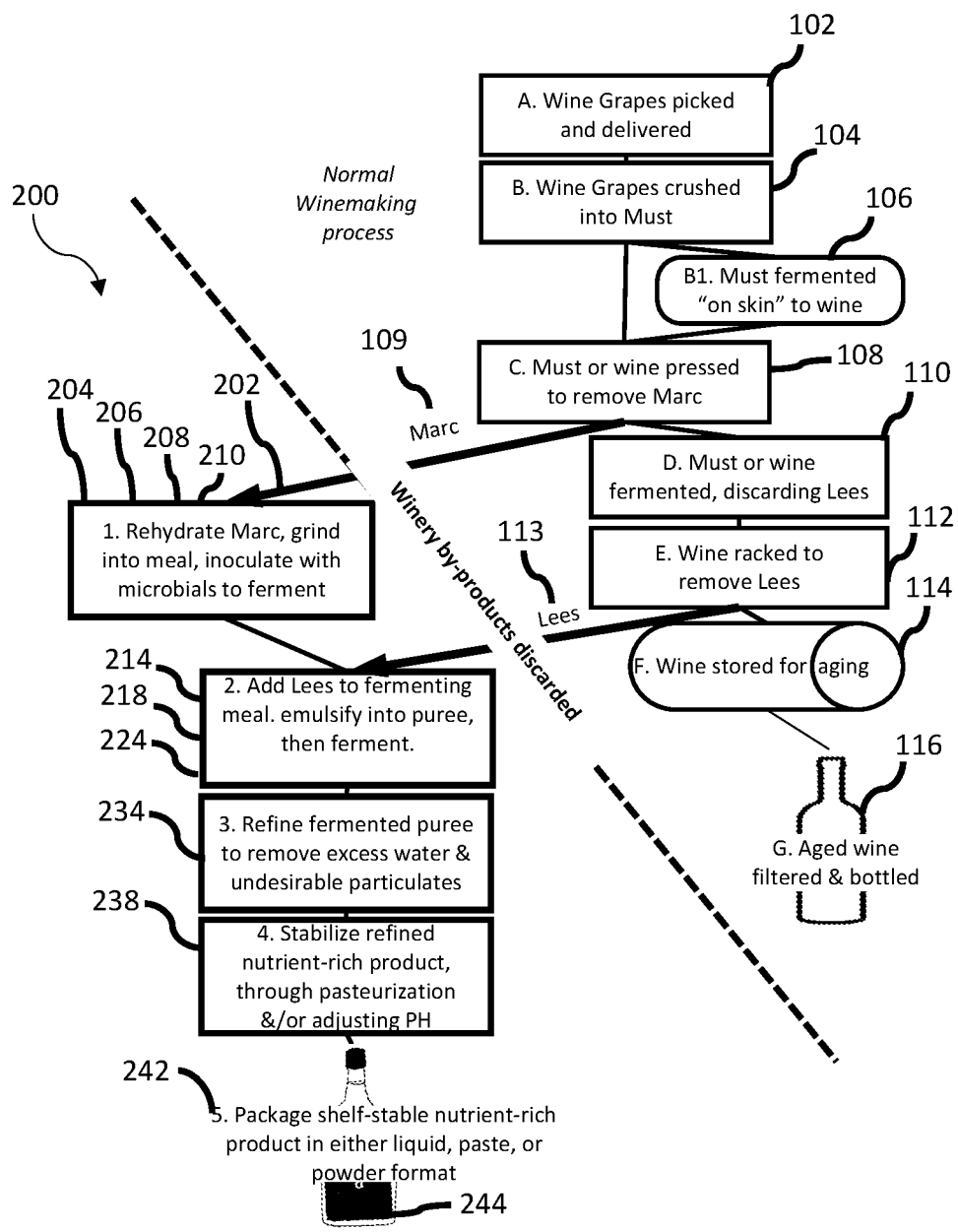
FIG. 2 illustrates one embodiment of the steps involved in separating marc and lees from a general winemaking process and inserting them into the system and processes described herein.
Figure 4:
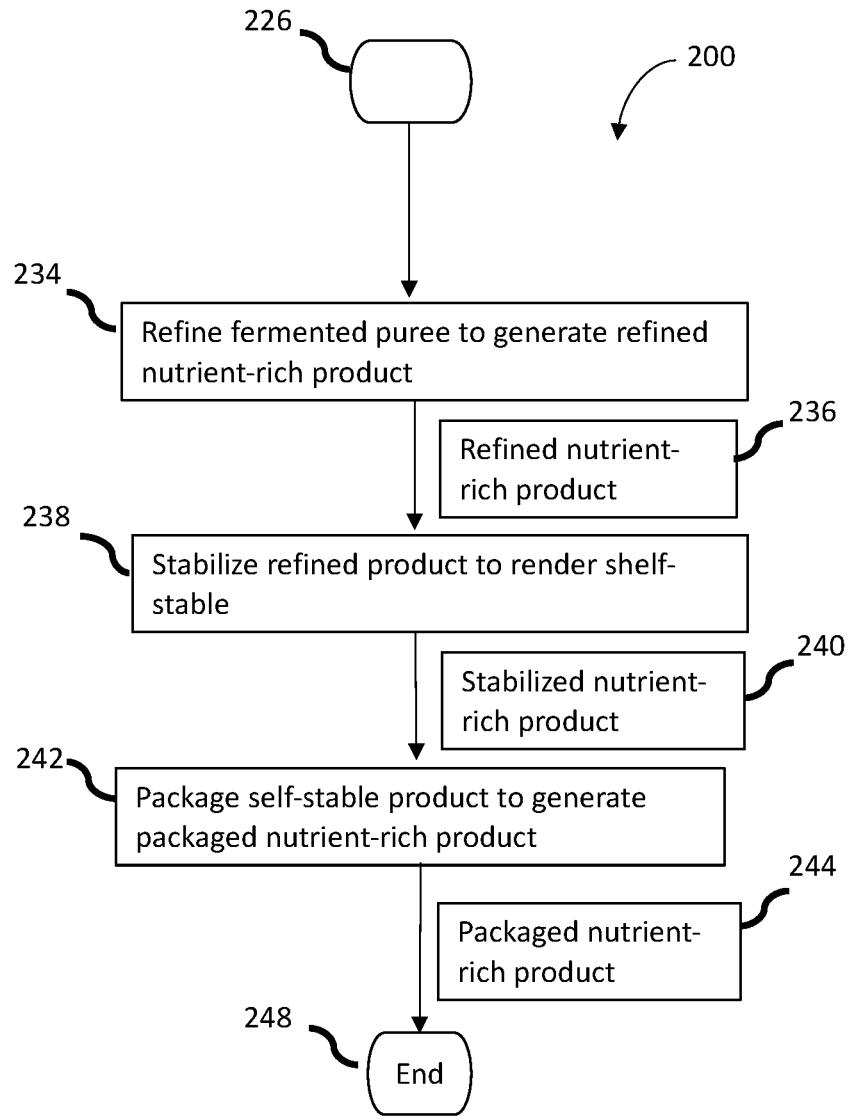
FIG. 4 is a continuation of the flow diagram of FIG. 3, continuing at 226.
Figure 5:
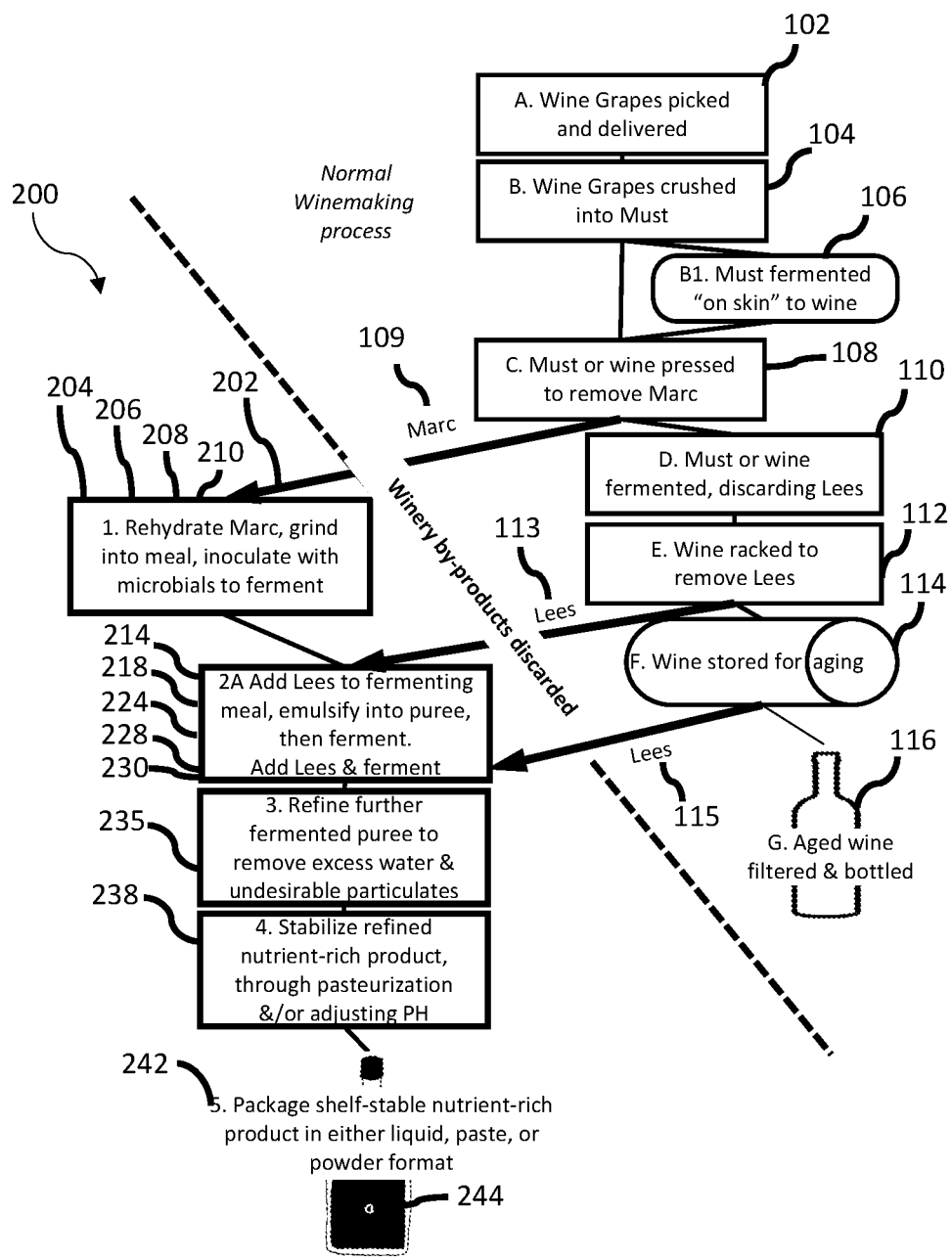
FIG. 5 provides one embodiment of the steps of separating marc and lees from a general winemaking process and inserting them into the system and processes described herein, wherein the process includes the addition off second-rack lees.

An Overview of the Derivative-Conversion Process Integrated with Winemaking Processes With reference to FIGS. 2 and 5, this section of the description will introduce an overview for two embodiments the derivative-conversion process alongside and integrated with a general description for wine making processes. The subsequent section, with reference to FIGS. 3, 4, 6 and 7, will describe further details of these steps, without reference to the general winemaking processes. One skilled in the art would appreciate and know that this system, methods, processes and nutrient-rich products made thereby 200 could be adapted for wineries producing fruit wine. In one embodiment, the system 200 is integrated with a winery that produces fruit wine. One embodiment, the system 200 is integrated with a winery that produces both grape wine and fruit wine. In one embodiment, the system, methods, processes and nutrient-rich products made thereby 200 include the derivatives produced by both the grape winemaking process and the fruit winemaking process.

With reference to FIGS. 2 and 5, embodiments of the process for making these bioactive nutrient-rich products are described below. The steps of a traditional general winemaking process are labeled with alpha characters (A, B, C, etc.). The steps within embodiments of the general derivative-conversion process for generating bioactive nutrient-rich products are labelled with numeric characters (1, 2, 3, etc.).

In Step A 102, the winery either picks or buys varietal wine grapes that are optimized for winemaking and they are transported to the winery "crush pad" to be processed. The grapes may be destemmed or not destemmed prior to Step B 104, depending upon the preferred method of wine production, and loaded into the grape crusher. During Step B 104, the grapes are masticated so that the juice (must) can be separated from the skins, pulp and seeds. If the crushed grapes and must are to be used in a white or rose style wine, they are immediately treated according to the process of Step C 108.

If the crushed grapes and must are to be used in a red or "orange" style wine, they are processed in Step B1 106, which entails loading the crushed grapes and must into the fermentation tank where yeast is added to initiate alcoholic fermentation. When the alcoholic fermentation process has terminated, the wine ("free run wine") and the crushed grapes are further processed in Step C 109. Typically, the free run wine is pumped off into tanks and the skins subjected to step C 108, where they are pressed to extract the remaining juice and wine. The press wine may optionally be blended with the free run wine at the winemaker's discretion.

Thus, Step C 108 is applied to either the must derived from Step B 104 (e.g, in the production of white wine) or to the alcoholic fermented wine (free run wine) derived from Step B1 106 (e.g., in the production of red wine). During Step C 108, the crushed grapes and either, the unfermented must derived from Step B 104 or the free run wine derived from Step B1 106, are loaded into the press so that the must or free run wine can be squeezed from the marc 109 (solid matter). The must, destined to become a white wine, is loaded into a fermentation tank where yeast may be added to initiate alcoholic fermentation of the must. The press wine produced from Step C 108, which has now been separated from the marc 109, in step D 110 is inoculated with specific strains of bacteria (lactobacter) to initiate malo-lactic fermentation to convert "crisp, green apple" malic acid to "soft, creamy" lactic acid to soften the taste of the wine. The marc 109, which is traditionally treated as food waste, is immediately removed from the "food preparation" area (crush pad).

Figure 3:
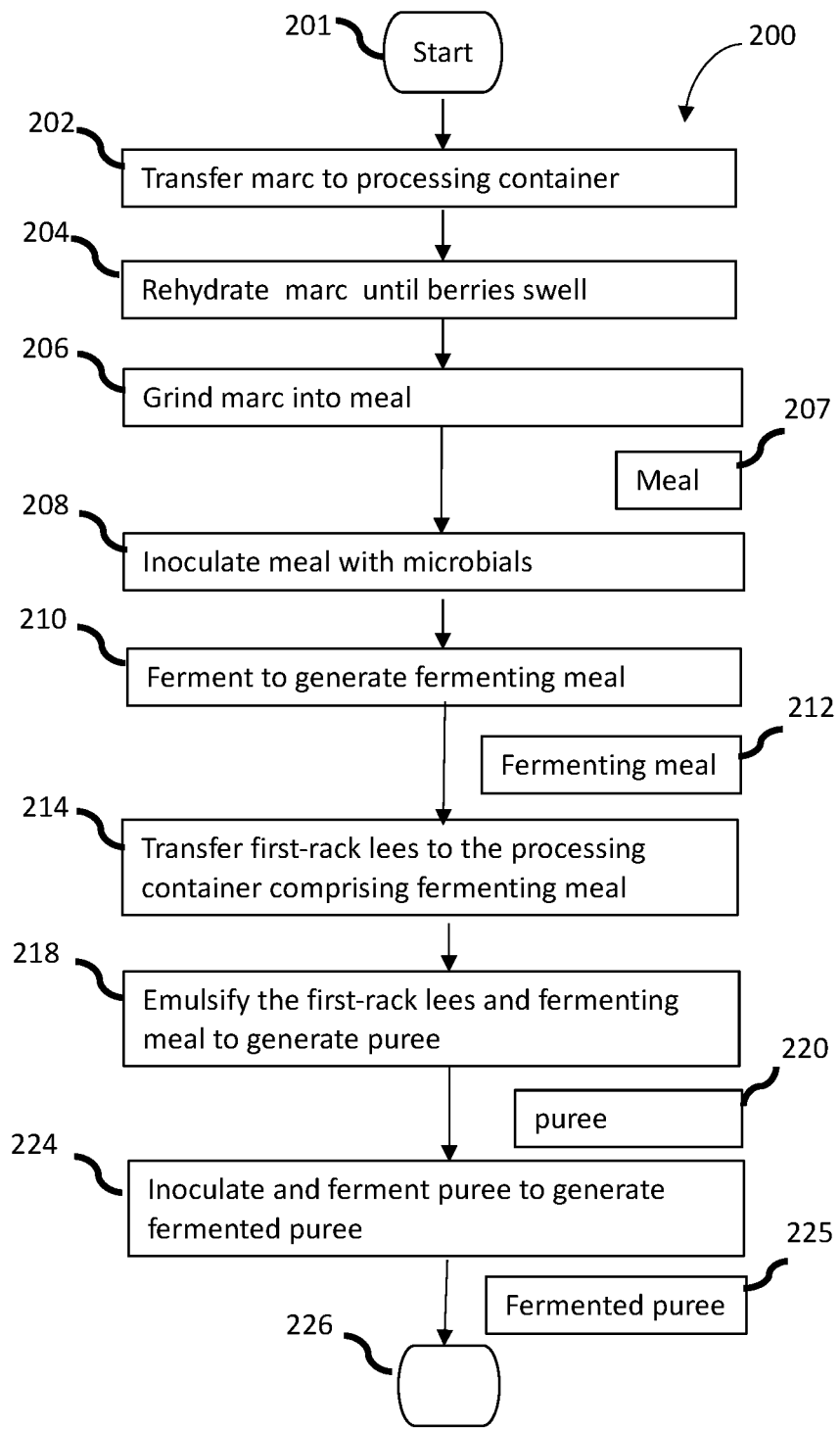
FIG. 3 is a flow diagram showing one embodiment of the steps of derivative conversion presented in FIG. 2, in addition to intermediates and nutrient-rich products generated throughout. As indicated at 226, the description of the process continues in FIG. 4.
Figure 6:
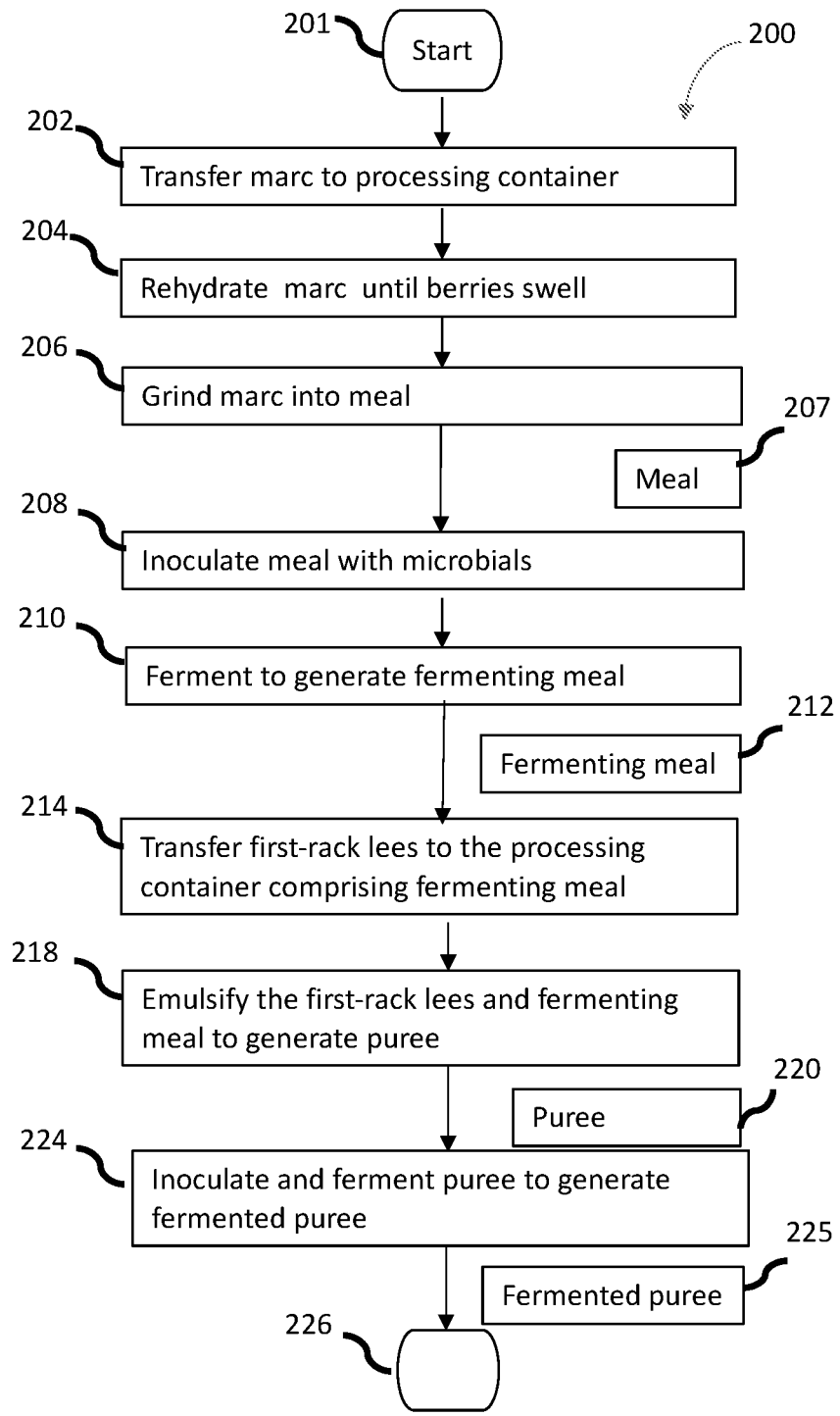
FIG. 6 is a flow diagram showing one embodiment of the steps of derivative-conversion presented in FIG. 5 in addition to intermediates and nutrient-rich products generated throughout. As indicated at 226, the description of the process continues in FIG. 7.

As illustrated by FIGS. 2 and 5, the process of derivative-conversion, begins by transferring marc 109 to one or more processing containers 300 (illustrated in FIG. 8) of this system to be processed during Step 1 204, 206, 208, 210 (illustrated in FIGS. 3 and 6). The marc 109 is rehydrated with enough water to saturate the marc 109. After the berries have swollen, the saturated marc is ground into fine particulates and is then inoculated with microbials to cause fermentation and dissolution of solid particles. This process can generally last for approximately 2 to 6 weeks before proceeding to Step 2 218, 224.

During Step D 110 of the general winemaking process for white wine, the must is fermented until it turns into wine. As part of this step the spent yeast, tartaric acid, skin and pulp particulates settles to the bottom of the fermentation tank. As mentioned above, the press wine is usually subjected to malo-lactic fermentation during Step D, during traditional red wine making practices.

During Step E 112 of the winemaking process, the settled particulates are separated from the wine by drawing the wine off of the top in a process known as racking and placed into oak, steel or ceramic vessels for aging. This particulate matter, suspended in a residual amount of wine is referred to herein as first-rack lees 113. During traditional winemaking, the first-rack lees 113 is typically treated as food waste and is immediately removed from "food preparation" area.

During the process of derivative-conversion, Step 2 214, 218, 224, incorporates the first-rack lees 113 into the processing container 300 where it is emulsified with the biomass, which is then further fermented.

During Step F 114 of winemaking, the wine is aged for 2 to 60 months, depending on the grape varietal and winemaking technique. The wine is then filtered to remove any residual lees, herein referred to as second-rack lees 115, and placed into bottles, kegs or waterproof boxes. During traditional winemaking, the second-rack lees 115 typically is treated as food waste and is immediately removed from the "food preparation" area. During the process of derivative-conversion, however, as illustrated in FIG. 5 the second-rack lees 115 can be transferred to the processing container 300 during Step 2A 214, 218 224, 228. 230, the biomass is then further-fermented to generate a further-fermented purée 232.

Thus, FIG. 2 illustrates that the first rack-lees 113 from Step E 112 is added to the emulsion created during Step 1 204, 206, 208, 210 mixed and then further fermented during Step 2 218, 224 until the fermented nutrient-rich product 226 achieves the desired flavour profile, nutrient value, and PH level. FIG. 5 illustrates that the first rack-lees 113 from Step E 112 is added to the emulsion created during Step 1 204, 206, 208, 210. mixed and then further fermented during Step 2 218, 224 until the second-rack lees 115 are ready, at which time they are transferred to the processing container and fermentation is continued until the further-fermented nutrient-rich product 232 achieves the desired flavour profile, nutrient value, and PH level.

FIGS. 2 and 5 describe that at Step 3 234, the fermented purée 225 or further-fermented purée 232 are refined using filtration, homogenization, other techniques, or a combination of techniques. At this step, excess water is removed along with any undesirable particulates or bi-nutrient-rich products, such as sulfur, bentonite, etc.

FIGS. 2 and 5 teach at Step 4 238 that refined nutrient-rich product 236 is rendered shelf-stable through pasteurization or correction of PH level through further fermentation and thereby converted to stabilized nutrient-rich product 240.

FIGS. 2 and 5 illustrate that during Step 5 242, the stabilized nutrient-rich product 240 is packaged into consumer, culinary and/or industrial vessels. It is then stored for shipment. The stabilized nutrient-rich product 240 could be in liquid, paste or powder format based on the needs of the end-user.

The Steps of the Derivative-Conversion Process Described in Greater Detail

FIGS. 4, 5, 7 and 8 outline the steps described above, including the sub-steps constituting the steps, intermediaries and nutrient-rich products involved in embodiments of the system, methods processes, and nutrient-rich products made thereby. For example, Step 1 204, 206, 208, 210 comprises four sub-steps and various intermediates. The details for each of the steps and sub-steps are described herein.

Step 1 Initial Acetic Acid Fermentation

Figure 7:
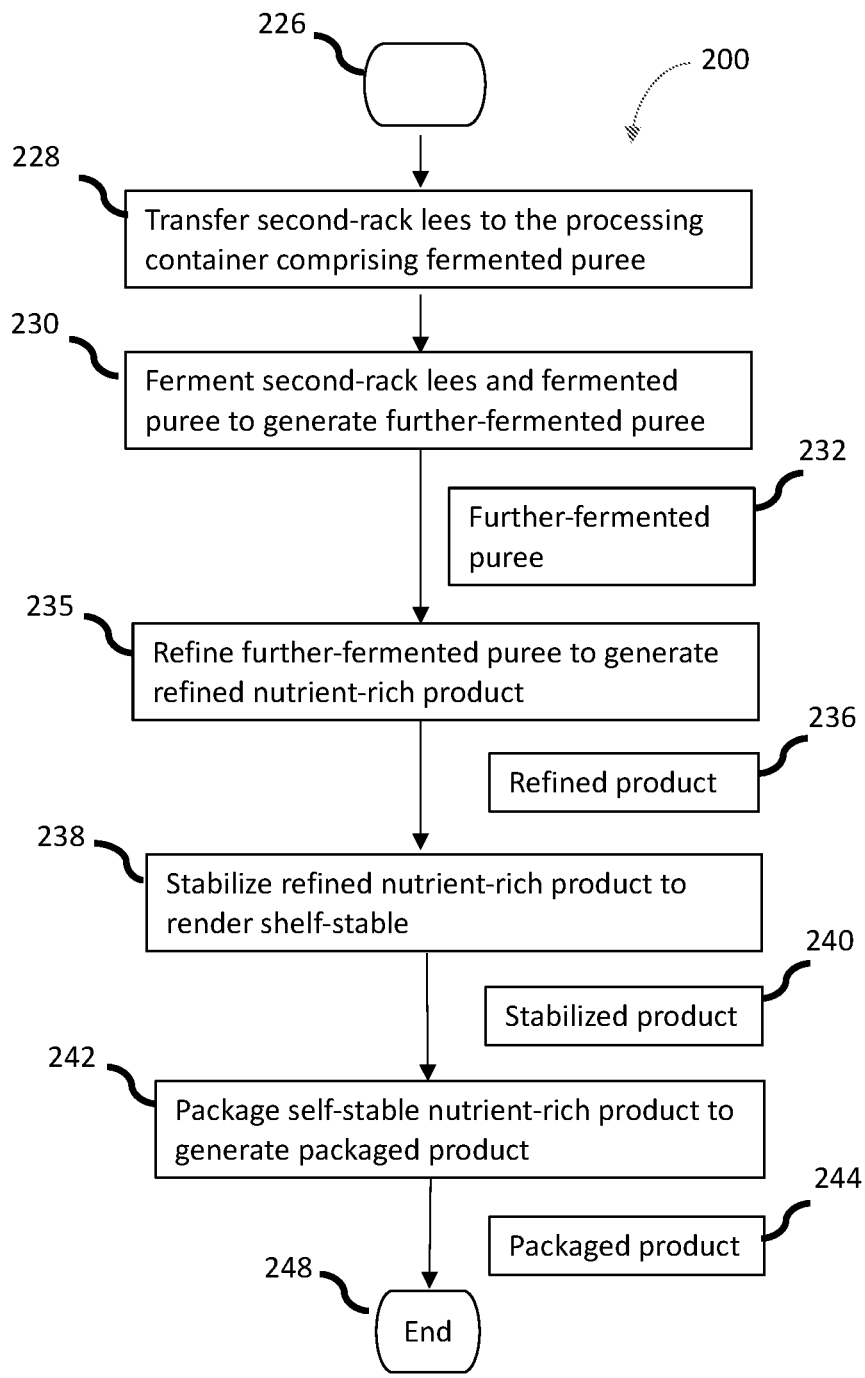
FIG. 7 is a continuation of the flow diagram of FIG. 6, continuing at 226.

As described in FIGS. 4 and 7, the marc 109 derived from the press is transferred to a processing container 300 of the system. Sub-step 202 is conducted by transferring the marc 109 from a collection vessel typically used in a winery to collect marc 109 from the press and pouring the contents into a processing container 300. The marc 109 is then rehydrated with an amount of water for a sufficient period of time to allow the berries to swell. In one embodiment, a processing container 300 is filled to 50-80% of its capacity, depending on the amount of marc available from the press. The addition space is reserved for lees and to provide sufficient air above the cap of the mixture to accelerate aerobic fermentation.

Once the berries have swollen, the biomass is ground into a meal 205. In one embodiment, the grinding process involves the use of a portable pureeing device that is inserted into the tank, which shreds the skins and pulp, and cuts up the seed, allowing the microbial "cocktail" to attack the grape skin particles, pulp, seed pulp and bruised husk. In one embodiment, a macerating pump, attached to the spigot that draws out the material, passing it though a grinder, and then pumping it back into the top of the container.

The meal 205 is then inoculated with a microbial culture that may comprise bacteria (e.g., acetic acid bacteria), enzymes and/or yeast to cause fermentation and dissolution of solid particles. Optionally, sugar or other natural sweetener may be added to accelerate the fermentation. The inoculated meal then is aeriated at a level that introduces enough oxygen to allow aerobic fermentation to dominate all bioactivity. The inoculated meal 205 is then allowed to rest and begin fermentation and thereby becomes fermenting meal 212. The processing containers are checked periodically to monitor the progression of fermentation as assessed by the pH, the Brix level, optionally the temperature. One skilled in the art of fermentation would know which factors would be most relevant to the type of nutrient-rich product they are seeking to generate.

This process can generally last for 2 to 6 weeks. As this system is integrated with the general winemaking process, as depicted in FIGS. 2 and 5, the time-period for this process can depend upon the availability of the lees generated by the winemaking process.

Step 2: Lee-Addition and Continued Fermentation

As described above, within the General Overview section, Step E 112 of the process of conventional winemaking, wherein either the must or pressed wine (red) is racked, generates first-rack lees 113. The first-rack lees 113 is typically considered food waste and immediately removed from the "food preparation" area. Wineries will either syphon the wine from the top of the fermentation tank until the wine becomes cloudy, or will drain the wine the wine from the bottom of the tank using a filtration system to remove lees particles.

First-rack 113 lees can be collected in food safe containers and then poured over the fermenting meal 212 in a processing container 300 during sub-step 214. During sub-step 218, the first-rack lees 113 and the fermenting meal 212 are emulsified to generate a purée 220. The purée is then fermented in sub-step 224, during which the pH of the purée will be expected to drop to below 3.5 pH.

Optional Inoculation of the Purée

One objective for this fermentation process is to establish how "sour" the ultimate fermented purée 225 should be allowed to become. Care must be provided regarding the levels of acetic acid present during the fermenting process. Ideally the optimal pH can be attained with the lactic acid remaining in the first-rack lees 113.

As described in the General Overview section, step D 110 of the general red winemaking process, involves inoculating the press wine produced from Step C 108, with specific strains of bacteria (lactobacter) to initiate malo-lactic fermentation to convert malic acid to lactic acid to soften the taste of the wine. If there isn't sufficient lactic acid remaining in the first-rack lees 113 after the malo-lactic fermentation, the purée 220 in processing container 300 is inoculated with a microbial solution comprising acetic acid bacteria during sub-step 224 and allowed to ferment for approximately 60-90 days.

The fermentation process is monitored by periodically checking the PH/Brix ratio to maintain the pH of the purée 220 below 4.5 pH. This stage of the process is considered finished when the pH drops to an appropriate level, likely around 3.5 or possibly less. and the purée 220 is considered completely converted to fermented purée 225. The processing containers are checked periodically to monitor the progression of fermentation as assessed by the pH, the Brix level, optionally the temperature. One skilled in the art of fermentation would know which factors would be most relevant to the type of nutrient-rich product they are seeking to generate.

Optional Storage-Lee-Addition Process

In one embodiment, illustrated in FIG. 5, an additional lee transfer step is included in the derivative-conversion process. During Step F 114 of the conventional winemaking process, the wine is stored for aging, which generates second-rack lees 115. This embodiment entails collecting and transferring the second-rack lees 115 to processing container 300 during sub-step 228.

This optional step is performed in a manner similar to the collection and transfer of the first-rack lees 113, described above. In this collection and transfer step, however, care must be taken to ensure that the winery did not employ any filtration catalysts, such as bentonite (clay), egg whites (non-vegan), that would contaminate the final nutrient-rich product. If these other substances are present, one skilled in the art would know what appropriate applications would work for the final nutrient-rich product that will eventually be produced and what should be avoided.

During sub-step 230, the processing containers are checked periodically to monitor the progression of fermentation as assessed by the pH, the Brix level, optionally the temperature, etc. One skilled in the art of fermentation would know which factors would be most relevant to the type of nutrient-rich product they are seeking to generate. Once the desired factors are present within the biomass, the further fermented purée 232 will be refined according to Step 3 324

Step 3: Raw Nutrient-Rich Product Refinement Process

During Step 3 234, the fermented purée 225 or optionally, the further-fermented purée 232 is refined using filtration, homogenization, other techniques, or a combination of techniques in order to convert the fermented purée 225 or the further-fermented purée 232 into a refined nutrient-rich product 236. At this step, excess water is removed along with any undesirable particulates or bi-nutrient-rich products, such as sulfur, bentonite, etc. One skilled in the art will appreciate the qualities and characteristics for the end nutrient-rich product, will know what criteria to look for at this stage of the process and will make the appropriate adjustments to generate an appropriate refined nutrient-rich product 236.

Some examples of steps that one skilled in the art may choose to employ include the following.

- During Step 3 234 the fermented purée 225 or the further-fermented purée 232 will first be tested for bentonite, sulphur and other food contaminants (likely before removal from the winery)
- In general, at this stage as described in more detail below during the work flow section, the processing container(s) 300 will be collected by the Business to continue processing within the business facility.
- If contaminants are present, the fermented purée 225 or the further-fermented purée 232 will be likely be processed in a different manner that will be used only for livestock feed or nutrient extraction.
- If sulphur is present, the fermented purée 225 or the further-fermented purée 232 is treated with a sulphur extractant (eg hydrogen peroxide) to remove the sulfur. It then would be homogenized, dewatered to a specific water %, and stored, usually by varietal.
- The stored material could optionally be blended with other varietals (if necessary) to achieve a consistent flavour and nutrient profile. There may be an optional homogenization step after blending to stabilize to purée (keep the water from separating). This step also may involve dewatering.

Once the objectives for the chemical characterization of the nutrient-rich product have been met, the material is considered to be final nutrient-rich product 236.

Step 4 Refined Nutrient-Rich Product Stabilization Process

During Step 4 238, the refined nutrient-rich product 236 is rendered shelf-stable through pasteurization or correction of PH level through further fermentation in order to convert the refined nutrient-rich product 236 into a stabilized nutrient-rich product 240. One skilled in the art will appreciate the qualities and characteristics for the end nutrient-rich product, will know what criteria to look for at this stage of the process and will make the appropriate adjustments to generate an appropriate stabilized nutrient-rich product 240.

There are applications for both a pasteurized purée (with no bioactive materials) and a probiotic purée. High-pressure pasteurization technology will normally be used to create a pasteurized nutrient-rich product, although other current or future pasteurization techniques may be employed. The bioactive purée will fermented to an approved pH level for sealed storage at room temperature, refrigerated temperature, and/or frozen.

Step 5: Nutrient-Rich Product Packaging Process

During Step 5 242 the stabilized nutrient-rich product 240 is packaged into consumer, culinary and/or industrial vessels in order to convert the stabilized nutrient-rich product 240 into a packaged nutrient-rich product 244. It is then stored for shipment. The stabilized nutrient-rich product 240 could be in liquid, purée, paste or powder format based on the needs of the end-user. One skilled in the art will appreciate the qualities and characteristics for the packaged nutrient-rich product 244, will know what criteria to look for at this stage of the process and will make the appropriate adjustments to generate an appropriate The stabilized nutrient-rich product 240 will be optimized for extrusion into sealed containers, which are specific to the industry and application using it. For example, the stabilized nutrient-rich product 240 may extruded into consumer-sized sealed jars or bottles to generate packaged nutrient-rich product 244 designed for home use. Alternatively, stabilized nutrient-rich product 240 may be extruded into 4 liter/1 gallon sealed containers to generate packaged nutrient-rich product 244 designed for culinary use. Alternatively, stabilized nutrient-rich product 240 may be extruded into sealed 20 liter/5 gallon pails, or 1000 liter Intermediate Bulk Containers to generate packaged nutrient-rich product 244 designed or industrial food processing or pharmaceutical use.

The Nutrient-Rich Product

The nutrient-rich product can be used in food preparation, to:

a. reduce the amount of sodium in a food formula
b. Preserve dairy, meat, condiment and cereal nutrient-rich products
c. Enhance the flavour of fruits, vegetables, and spices within a food formula
d. Provide significant nutrient value to a food formula
e. Provide a source of yeast and other bacteria to cause the leavening of bread
f. Provide a source of bacillus to cause the fermentation of dairy nutrient-rich products
g. Provide a source of bacillus to cause the fermentation of plant-based proteins The nutrient-rich product may also be used to provide a medium for extraction of nutrients for pharmaceutical use in addition to provide a medium for topical applications in cosmetics or skin therapy.

Acetic Acid Bacteria

The steps of the derivative-conversion require inoculation of microbial formulation, comprising acetic acid bacteria. One skilled in the art of fermentation would know which one(s) to select from the family of family Acetobacteraceae.

Acetic acid bacteria (AAB) are a group of rod-shaped, Gram-negative bacteria which aerobically oxidize sugars, sugar alcohols, or ethanol with the production of acetic acid as the major end nutrient-rich product. This special type of metabolism differentiates them from all other bacteria. The acetic acid bacteria consist of 10 genera in the family Acetobacteraceae, including *Acetobacter*. Species of *Acetobacter* include: *A. aceti; A. cerevisiae; A. cibinongensis; A. estunensis; A. fabarum; A. farinalis; A. indonesiensis; A. lambici; A. liquefaciens; A. lovaniensis; A. malorum; A. musti; A. nitrogenifigens; A. oeni; A. okinawensis; A. orientalis; A. orleanensis; A. papaya; A. pasteurianus; A. peroxydans; A. persici; A. pomorum; A. senegalensis; A. sicerae; A. suratthaniensis; A. syzygii; A. thailandicus; A. tropicalis*; and *A. xylinus*. Several species of acetic acid bacteria are used in industry for production of certain foods and chemicals.

The strains, which have been identified include: Acidibrevibacterium *Acidicaldus Acidiphilium Acidisoma Acidisphaera Acidocella Acidomonas Ameyamaea Asaia Belnapia Bombella Caldovatus Commensalibacter Craurococcus Crenalkalicoccus*; *Dankookia Elioraea Endobacter Gluconacetobacter*; *Gluconobacter Granulibacter Humitalea Komagatabacter Komagataeibacter Kozakia Muricoccus Neoasaia Neokomagataea Nguyenibacter Paracraurococcus*; Parasaccharibacter. Although a variety of bacteria can produce acetic acid, mostly members of *Acetobacter, Gluconacetobacter*, and *Gluconobacter* are used commercially. One skilled in the art would know which one(s) to choose for the fermentation processes depending on the final nutrient-rich product they desire to generate.

Lactic Acid Bacteria

Lactic acid bacteria (LAB) are an order of gram-positive, acid-tolerant, generally nonsporulating, non=respiring, either rod-shaped (bacilli) or spherical (cocci) bacteria that belong to the order Lactobacillales and share common metabolic and physiological characteristics. Lactic acid bacteria are used in the food industry for a variety of reasons such as the production of cheese and yogurt nutrient-rich products. The genera that comprise the LAB are at its core *Lactobacillus, Leuconostoc, Pediococcus, Lactococcus*, and *Streptococcus*, as well as the more peripheral *Aerococcus, Carnobacterium, Enterococcus, Oenococcus, Sporolactobacillus, Tetragenococcus, Vagococcus*, and *Weissella*.

The Processing Container

Figure 8:
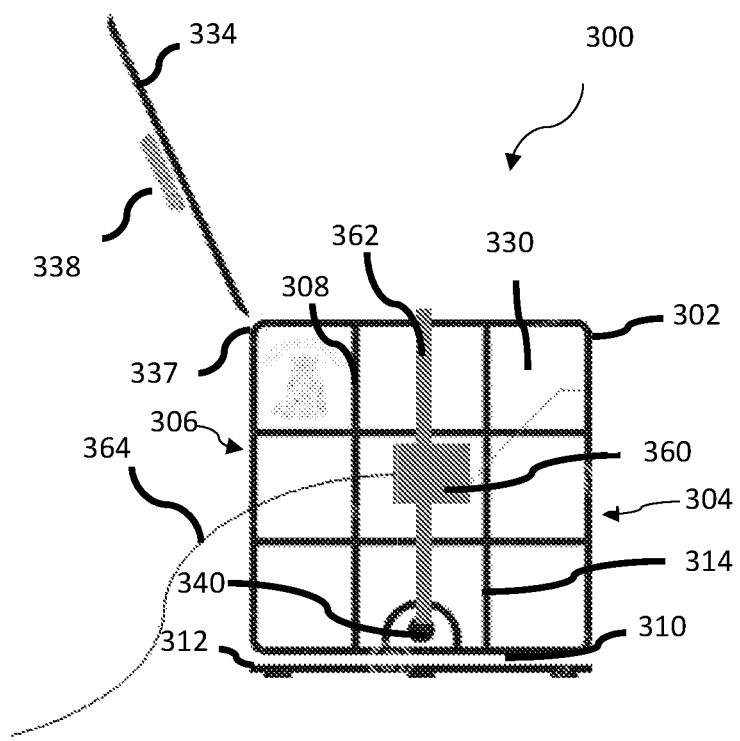
FIG. 8 illustrates one embodiment of a processing container within this system.

One embodiment of the processing container 300 is depicted in FIG. 8. The processing container 300 is a version of a food-grade intermediate bulk container (IBC), commonly referred to as an IBC tote, with a holding capacity of about 1,040 or 1,250 litres (275 and 330 US gal), capable of being stacked, which has been appropriately modified for use with the methods and processes within this system 200.

One embodiment of a processing container 300 comprises and inner compartment 330 and an outer support structure 302. The outer support structure has four "walls" or cage-walls, (front 304, back 306, right 308, left not shown or referenced), a rectangular base 310, which are all interconnected. The outer walls may be solid or cage-like, the latter which is described in this non-limiting embodiment. The base 310 may incorporate the function of a pallet 312 into the structure of the outer base 310 of the support structure.

The inner compartment 330 has four walls (only the right side is visible in FIG. 8), a retractable lid 334. which is attached via hinging means 337 and attached to the back wall of the inner compartment 330 of the processing container 300. A top access port 338 may be attached to the retractable lid 306, providing entry into the inner compartment 330, without having to retract the lid 334. The inner compartment 330 has a lower access port 340, providing entry into the lower portion of the inner compartment 330.

The container has an aerator 360, attached to support means 362, that gains access to the biomass through the lower access port 340, and forces air into the bottom of the container allowing air to percolate up through the mixture, encouraging aerobic fermentation. The aerator 360 could either be powered via external electric power means 364 or solar/battery power (not shown).

Optionally, multiple sensory devices to monitor temperature, pH level and Brix, as well as other fermentation activities could be attached to the container, and could optionally be monitored by using WiFi. The optional monitors would either be powered via external electric power or solar/battery power.

The advantage of modified IBC totes is that most wineries already use unmodified totes and have equipment that allows them to move and stack them on their property. The modified totes can be sealed to minimize food contamination and placed in an external part of the property, either in or adjacent to the vineyard. One of the advantages of in-vineyard placement is $CO^2$ sequestering by the vines and undergrowth.

One or more processing container(s) 300 are delivered to a winery for integration into their winemaking and processing facilities and processes prior to crush. The numbers of containers 300 would be based on the following ratio. Anticipated red grape tonnage x 25%, which is the average percentage of marc 109 generated during Step C 108.

The Business Method

There are a number of different ways that the business method could be structured to appropriately integrate the system, method, and processes described herein in with the processes and facilities of a winery.

Figure 12:
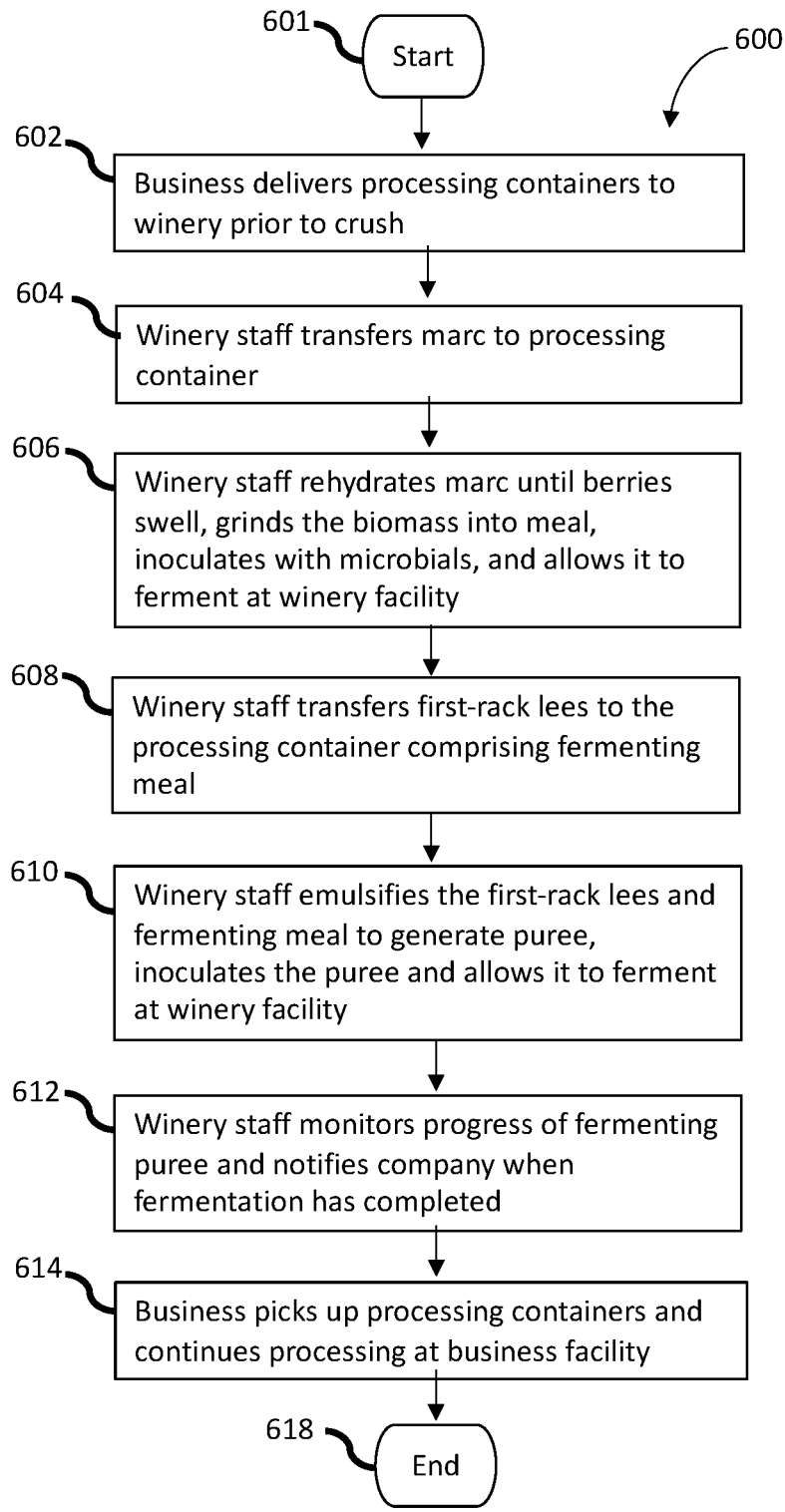
FIG. 12 provides one embodiment of a method of performing the business method described herein.

One embodiment as outlined in FIG. 12, entails the following steps. At step 602, a business delivers one or more processing container(s) 300 to a winery prior to crush. At step 604, winery staff transfers marc to one or more processing container(s) 300. At step 606, winery staff rehydrates marc until berries swell, grinds the biomass into a meal, inoculates with microbials, and allows it to ferment at the winery facility. At step 608 winery staff transfers first-rack lees to the one or more processing container(s) 300 comprising fermenting meal. At step 610 winery staff emulsifies the first-rack lees and fermenting meal to generate purée, inoculates the purée and allows it to ferment at winery facility. At step 612 winery staff monitors the progress of fermenting purée and notifies the company when the fermentation has completed. At step 614, the business picks up the one or more processing container(s) 300 and continues processing the fermented purée at the business facility.

In one embodiment, the business and the winery may choose to further process the fermented purée at the winery facility. In one embodiment, the business may choose to pick-up the processing containers prior to adding the first-rack lees 113, and conduct the further steps at the business facility. In this embodiment, the business may choose to collect the first-rack lees 113 from the winery when it is ready and add it to the fermenting meal 212 in the processing container(s) 300 at the business facility. One skilled in the art would appreciate that there are many different ways that this business relationship could be structured to optimize the resources of the business and the winery, such that these embodiments are considered to be non-limiting examples of how the work-flow of the business relationship could be designed.

One embodiment as described in Example 1, entails the business delivering processing containers to a winery prior to Step A 102 of the winemaking process, and retrieving them after fermentation has been completed and fermented purée 225 has been generated within processing container(s) 300. The business benefits by having the initial steps of the process conducted on site at the Winery. This point saves the business from having to construct facilities on its location for Steps 1 and 2, and can focus the design of the Business facilities to processing the various nutrient-rich products under GRAS Conditions.

The business could pay the winery for:
a) The amount of properly fermented purée potentially adjusted for:
  1. Level of solids with purée
  2. Type of varietal grapes used in the purée
  3. Whether the grapes are organic
  4. From a publicly recognized premium district, estate or vineyard
  5. Distance from the processing center
b) Additional work or services independent of the amount of purée acquired, such as providing electrical power to the location or providing access to vineyard property during off hours.
c) Participating in nutrient-rich product development field testing.

In addition, the winery benefits by:
a) reduction of waste and costs associated therewith;
b) possibly the acquisition of Carbon Credits
c) an additional revenue stream;
d) incorporation of named winery purée into premium foods; and
e) eliminating methane emissions caused by disposal in buried landfills The winery also benefits by diverting the substances from waste management and disposal processes to the conversion process, because these bioactive by-products are subject to numerous local health, environmental and worker safety regulations in the post-production treatment and disposal. The impact of these regulations on the winery are minimized.

Example I

With reference to Table 1 presented in FIG. 11, this example describes one non-limiting manner in which the system, methods, processes and nutrient-rich products 200 made thereby can be incorporated into a winery producing grape wine. The Business is used to denote the business practicing the business methods described herein. The Winery is used to denote the wine production business within which this system, methods, and processes 200 is integrated.

Phase I. At the Winery

Table 1 shows the main stages in column 1, wherein the employees of the Winery (referred to herein as "cellar-hand") are instructed to perform task(s) involved in the processes of this system, methods, processes 200. The Business activities are presented in column 2, the Winery's activities in column 3, and estimated cellar-hand time per container in column 4. It is estimated that cellar-hand activities will be less than one hour per container over the ≈140 days that the containers are on site at the Winery.

Stage I. Pre-Crush
The Business drops processing containers 300 at the winery prior to crush. The processing container 300 may already have an initial microbial cocktail encased in the interior compartment of the processing container 300, which will become activated once water is added to the processing container 300.

The numbers of processing containers 300 could be based on the following ratio: anticipated red grape tonnage x 25% (average percentage of marc 109). For example, if a winery accepts 100 tons of red grapes, the Business could deliver 25 processing containers 300. Empty processing containers 300 could be stacked 2-3 high in a place where they least impact crush activities. One non-limiting example of where empty processing containers 300 could be stored on the grounds of the Winery is illustrated in FIG. 1.

Stage II During Press (Crush): Transfer Marc to Processing Container

Pursuant to sub-step 202, the cellar-hand is instructed to collect, transfer and deliver marc 109 generated during Step B 104 (crush), using a collection bin that is normally used to collect marc 109 from the press. Rather than discarding the marc 109 as per the usual winemaking process, wherein the marc 109 is usually dumped into a steel disposal bin, the cellar-hand is instructed to place the marc 109 into processing containers 300. The cellar-hand is instructed to fill the processing container 300 until the marc 109 fills up to the 800-ltr level of the processing container 300, and then instructed to add sufficient water to saturate and cover the marc 109, allowing the berries to swell as per sub-step 204, and to close and secure the lid 334. This step generally requires less than 6 minutes to for the cellar-hand to perform, which is slightly longer than if they were to dump the marc 109 into a disposal bin as per the traditional process. After the berries have swelled, the hydrated marc may be optionally macerated using a motorized high-sheer mixer that would break the seeds and skin. This accelerates the fermentation process and seed decomposition. This step may be delayed until after the lees are added.

Figure 9:
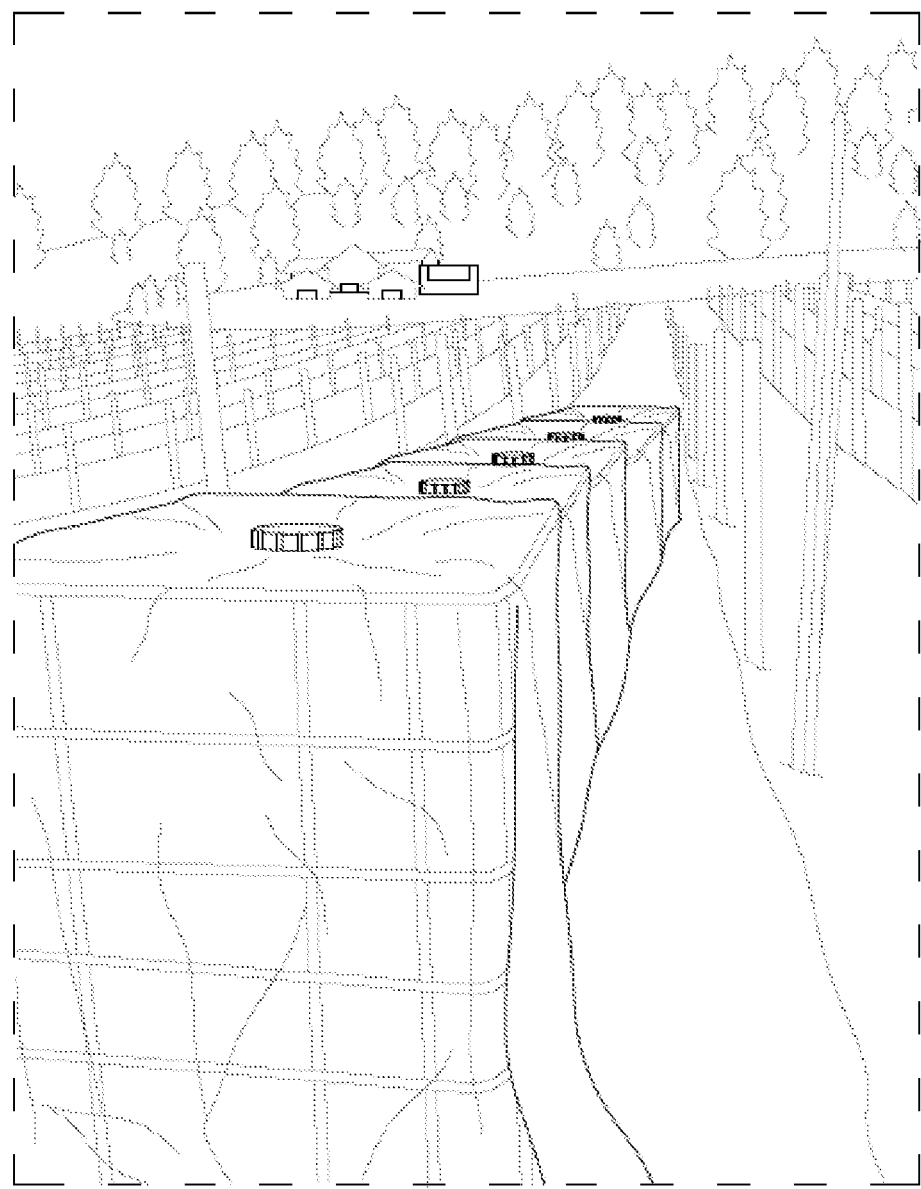
FIG. 9 shows one example of one embodiment of the integration of a series of processing containers into the vineyard of a winery facility, which includes one or more protective covers.
Figure 10:
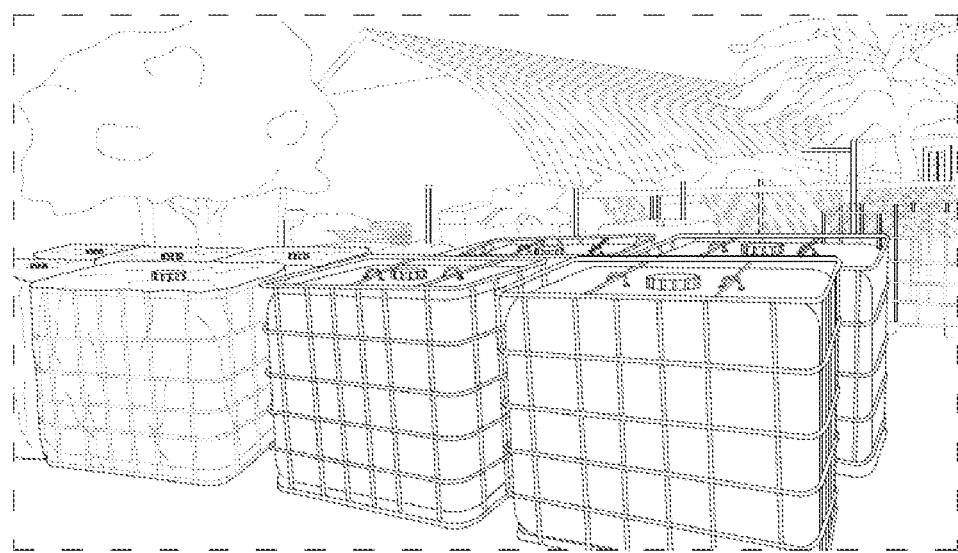
FIG. 10 shows one example of one embodiment of the placement of a series of processing containers on a winery property.

If necessary, the cellar-hand can move and/or restack the processing containers 300 to minimize the impact of the presence of processing containers 300 on space requirements of the crush activities. One example of where processing containers 300 can be placed is illustrated in FIGS. 1, 9 and 10. The biomass in the processing containers 300 is allowed to rest and begin fermentation from natural bacteria and/or added microbials, while waiting for first-rack lees 113.

Stage III: Transfer First Rack Lees to Processing Container

When Step E of the winemaking process is completed, the cellar-hand is instructed to collect and transfer the first-rack lees 113 to the processing container(s) 300, pursuant to sub-step 213 of the process. The time estimate for performing sub-step 213 is approximately 1-2 minutes x 19 ltr (five gallon) pails per container, which is generally takes less amount of time than the usual time required to dispose of first-rack lees 113. Once the lees are mixed into the marc, the combined material can be macerated using a high-sheer mixer, either for the first time if this did not happen in Stage II, of as secondary maceration to further break down the purée.

Stage IV: Prior to Microbial Fermentation

After sub-step 224 has been performed, the cellar-hand is instructed to place processing container(s) 300 together in vineyard row(s) reasonably close to an electric power source. The cellar-hand is instructed to place processing container(s) 300 where it would be convenient. and where $CO_2$ sequestering could be maximized. The more containers that are lined up, the better as they will maintain internal heat. A protective cover could then be placed over a series of the containers. The cover will be tamper-resistant, will capture solar heart, and will retain heat from both the fermentation process and solar capture. They can also be used as a windbreak if desired. One example of where processing containers 300 can be placed is illustrated in FIGS. 1, 9 and 10. The cellar-hand is instructed to let processing container(s) 300 ferment for 60-90 days.

Stage V. During Microbial Fermentation

During this fermentation period, the cellar-hand is instructed to periodically check the PH/Brix measurements of the fermenting purée in the processing container(s) 300. Should the purée in a specific container show signs of stabilization (pH and BRIX levels stay constant for an extended period), the winery would advise the Business of the situation.

Stage VI Post Microbial Fermentation

When the fermentation has been deemed to be finished, the Business picks up the processing container(s) 300 for processing at the Business facility. The cellar-hand will generally assist in this process, for example, using winery forklifts to transfer the processing container(s) 300 to the Business truck. This is likely 90-120 day after marc 109 is pressed. For example, if Merlot were pressed on November 1, the container could be ready between February 1 and March 1. If Cabernet Sauvignon grapes were pressed December 1, the processing container 300 would be ready for pick-up by the Business approximately March 1-April 1. The processing container 300 would be ready for shipment from the winery to the Business at this time.

Phase II: At the Business Facility

The fermented purée 225 is processed at the Business facility using Business staff. In brief, the steps generally include that Business staff:

transfers the processing containers to Business facility;
empties the contents of processing container(s) 300 into a blending tank with other varietals to achieve a consistent blend;
emulsifies and homogenize the fermented purée 225 to mitigate and/or remove oversized grape seed husk;
packages stabilized nutrient-rich product 240 new processing container(s) 300; and
ship packaged nutrient-rich product 244 to one or more food processor(s)

The invention claimed is:

1. A method of converting post-crush winery derivatives into nutrient-rich products comprising the steps of:
   a. a business delivers a container to a winery prior to crush;
   b. winery staff is directed by the business to transfer marc containing crushed fruit to said container;
   c. the business picks up the container comprising the crushed fruit and conducts further processing steps at another location, comprising:
      i. rehydrating the marc,
      ii. inoculating the marc with microbials, and fermenting until the pH drops to a value in the range of 3.5 to 4.5; and
      iii. grinding the fermented marc to generate a puree.

2. The method of claim 1, wherein step c further includes filtering the fermented puree.

3. The method of claim 2, wherein step c further includes transferring said filtered fermented puree to a blending tank and blending said filtered fermented puree with filtered fermented puree of one or more other varieties.

4. The method of claim 3, wherein step c further includes grinding the blended fermented puree with a high shear mixer.

5. The method of claim 4, wherein step c further includes stabilizing the blended fermented puree.

6. The method of claim 4, wherein step c further includes drying the blended fermented puree.

7. The method of claim 5, wherein step c further includes packaging the stabilized fermented puree.

8. A nutrient-rich product produced by a method for converting post-crush marc derived from winemaking into a refined product that comprised the following steps:
   a. a container was provided by a business at a winery prior to crush;
   b. the winery staff directed by the business transferred marc containing crushed fruit into said container;
   c. further processing steps comprised;
      i. the marc was rehydrated,
      ii. the rehydrated marc was inoculated with microbials, and fermented until the pH dropped to a value in the range of pH 3.5 to pH 4.5; and
      iii. the fermented marc was ground to generate a puree.

9. The nutrient-rich product of claim 8, wherein step c further included filtering the fermented puree.

10. The nutrient-rich product of claim 8, wherein step c further included transferring said filtered fermented puree to a blending tank and blending said filtered fermented puree with filtered fermented puree of one or more other varieties.

11. The nutrient-rich product of claim 10, wherein step c further included grinding the blended fermented puree with a high shear mixer.

12. The nutrient-rich product of claim 11, wherein the step c further included stabilizing the blended fermented puree.

13. The nutrient-rich product of claim 12, wherein step c further included dewatering the blended fermented puree.

14. The nutrient-rich product of claim 13, wherein the product is in the form of a paste.

15. The nutrient-rich product of claim 13, wherein the product is in the form of a powder.

16. A method of converting winery derivatives into nutrient-rich products comprising the steps of:
   a. a business delivers a container to a winery prior to crush;
   b. winery staff is directed by the business to transfer marc containing crushed fruit to said container;
   c. marc containing crushed fruit is processed, comprising the steps of:
      i. rehydrating the marc;
      ii. inoculating the marc with microbials; and fermenting the marc at the winery facility until the pH drops to a value in the range of pH 3.5 to pH 4.5; and
      iii. the fermented marc is ground to generate a puree.

17. The method of claim 16, wherein steps c.i and c.ii, are performed by winery staff under the direction of the business, who rehydrates the marc, inoculates with microbials, and allows it to ferment at the winery facility.

18. The method of claim 17, wherein winery staff under the direction of the business, monitors the progress of fermenting puree and notifies the business when the fermentation has completed.

19. The method of claim 16, wherein steps c.i and c.ii, are performed by the business, who rehydrates the marc, inoculates with microbials, and allows it to ferment at the winery facility.

20. The method of claim 19, wherein the business monitors the progress of the fermenting puree and picks up the container when the fermentation has completed.

\* \* \* \* \*